United States Patent [19]

Parron et al.

[11] Patent Number: 5,783,727
[45] Date of Patent: Jul. 21, 1998

[54] PRODUCTION OF 2,6-TOLUYLENE DIISOCYANATE FROM A MIXTURE COMPRISING 2,6-TOLUYLENE DIISOCYANATE AND 2,4-TOLUYLENE DIISOCYANATE

[75] Inventors: Jean-Claude Parron, Caluire; Denis Revelant, Genas; Francois Vachet, Decines, all of France

[73] Assignee: Rhone-Poulenc Chimie, Courbevoie, France

[21] Appl. No.: 716,292
[22] PCT Filed: Mar. 24, 1995
[86] PCT No.: PCT/FR95/00366
§ 371 Date: Jan. 21, 1997
§ 102(e) Date: Jan. 21, 1997
[87] PCT Pub. No.: WO95/26332
PCT Pub. Date: Oct. 5, 1995

[51] Int. Cl.⁶ .................................................. C07C 249/00
[52] U.S. Cl. ............................................................ 560/352
[58] Field of Search ................................................ 500/352

[56] References Cited

U.S. PATENT DOCUMENTS 2,831,012   4/1958   Bernard .................................. 260/453
3,591,617   7/1971   Buchsbaum ........................... 260/453

*Primary Examiner*—Samuel Barts
*Attorney, Agent, or Firm*—John A. Shedden; Jean-Louis Seugnet

[57] ABSTRACT

A method for obtaining substantially pure toluylene 2,6-diisocyanate from a mixture of the 2,4 and 2,6 isomers of toluylene diisocyanate, wherein at least one crystallizing-melting cycle is performed on the mixture of said isomers to separate out the toluylene 2,6 diisocyanate isomer. In an alternative embodiment, the mixture is contacted, prior to the crystallizing-melting cycle, with a compound or catalyst capable of converting part of the toluene 2,4-diisocyanate isomer therein, and the reacted 2,4 isomer is separated. Said method is advantageous in that usable by-products are produced.

18 Claims, No Drawings

PRODUCTION OF 2,6-TOLUYLENE DIISOCYANATE FROM A MIXTURE COMPRISING 2,6-TOLUYLENE DIISOCYANATE AND 2,4-TOLUYLENE DIISOCYANATE

This application is a 371 of PCT/FR95/00366 filed Mar. 24, 1995.

The present invention relates to a process for the production of 2,6-toluylene diisocyanate from a mixture of the 2,4- and 2,6-isomers of toluylene diisocyanate.

The 2,4- and 2,6-isomers of toluylene diisocyanate (TDI hereinafter) are very important compounds which form the basis of the development of polyurethanes, which have many applications. Thus, these polymers may be used to manufacture flexible foams, among the main applications of which are household furniture and car seating. They may also be used for the manufacture of high-performance elastomers and enter into the composition of one- or two-component paints.

Most of the industrial applications of TDI use the 2,4- and 2,6-isomers as a mixture. The mixture most commonly used comprises 80% of the 2,4- isomer and 20% of the 2,6-isomer. The use of the 65/35 2,4-/2,6-isomer mixture is also known, although more restricted, in the field of high-lift flexible foams, for example.

However, polyurethanes synthesized from pure isomers have particularly advantageous properties when compared with those obtained from mixtures of these isomers. Thus, 2,6-TDI has noteworthy properties when it is used as a component in the synthesis of elastomers. The reason for this is that, in the particular case of polyester or polycaprolactam systems coupled with diamines, 2,6-TDI strongly improves the tear strength as well as the resistance to tear propagation. In addition, the hardness and resilience are improved and the modulus is increased from 100 to 200%. When diols are used as coupling agents, the tear strength and the resistance to tear propagation are also considerably improved.

There is consequently great value in obtaining the 2,6-TDI isomer pure. Various routes are known for gaining access to this product. Mention may be made in particular of chromatographic separation techniques, in which the mixture is treated on a column filled with zeolite, for example. These methods may be used directly on both TDI isomers, and they may likewise be used to separate the precursors of these compounds, such as, for example, the 2,4- and 2,6-isomers of dinitrotoluylene or of diaminotoluylene.

There are, however, drawbacks to proceeding in this way. Indeed, these techniques make it necessary to work with very dilute amounts of mixture and require the use of rigorously anhydrous solvent. However, the presence of traces of water is quite often inevitable and these traces react with the isocyanate groups to produce urea. This consequently results in the column being of reduced efficiency, or even becoming blocked. In addition, when the TDI precursors are treated, it is necessary subsequently to have available independent industrial means which allow each of the compounds purified to be converted into isocyanate.

The aim of the present invention is thus to propose a process for the production of the 2,6-TDI isomer which does not have the abovementioned drawbacks.

Moreover, the process according to the invention has the advantage of giving by-products which can be upgraded, in particular in the standard applications of isocyanates.

Thus, the subject of the present invention is a process for the production of a 2,6-TDI isomer from a mixture of 2,4- and 2,6-TDI isomers, in which the said mixture, comprising at least 50% 2,6-TDI isomer, is subjected to at least one cycle of crystallization-melting.

The subject of the invention is moreover a process for the production of a 2,6-TDI isomer from a mixture of 2,4- and 2,6-TDI isomers, in which the said mixture, comprising at least 50% 2,4-TDI isomer, is placed in contact with a compound or a catalyst capable of converting some of the 2,4-TDI isomer present, and in that the 2,4-isomer which has reacted is separated out, then the resulting mixture is subjected to at least one cycle of crystallization-melting.

Other advantages and characteristics of the invention will emerge more clearly on reading the description and the examples which follow.

The 2,4- and 2,6-TDI isomer mixture which can be treated in accordance with the process according to the invention advantageously comprises any proportion between the two isomers.

According to a first variant of the process of the invention, the treated mixture comprises at least 50% 2,6-TDI isomer.

In this case, the mixture is subjected to one or more crystallization-melting cycles, the process of which will be described in detail later.

According to a second variant of the process according to the invention, the mixture to be treated comprises at least 50% of the 2,4-TDI isomer.

In this case, prior to the cycles of crystallization-melting, the mixture to be treated is placed in contact with a compound or a catalyst capable of converting some of the 2,4-TDI isomer present, and in that the 2,4-isomer which has reacted is separated out.

This variant of the process is particularly advantageous inasmuch as it allows the treatment of mixtures obtained directly from the phosgenation of the corresponding amines or from the hydrogenation reaction of the corresponding dinitrotoluenes, followed by the phosgenation of the resulting amines. For example, mixtures comprising 80% 2,4-TDI and 20% 2,6-TDI, or alternatively 65% 2,4-TDI and 35% 2,6-TDI, are suitable for carrying out the invention.

Thus, in the case of this second variant, the process according to the present invention may be separated into two distinct parts, the first relating more particularly to the conversion of the 2,4-TDI isomer and the second to the production of the 2,6-TDI isomer, advantageously in substantially pure form.

The first part of the process as defined above thus consists in converting the 2,4-TDI so as to be able to separate the products obtained from the 2,6-TDI isomer.

Given the reactivity of the two isomers, the 2,4- isomer will be converted first. However, despite the considerable selectivity of the reactions involved with respect to the 2,4-isomer, it cannot be excluded that a part, albeit a considerably smaller part, of the 2,6-isomer also reacts.

For reasons of simplicity, in the following text, reference will be made only to the conversion of the 2,4- isomer, bearing in mind that some of the 2,6-isomer may have been converted.

Two types of reaction can conveniently be used to convert the 2,4- isomer.

Thus, the mixture to be treated can be placed in contact with a catalyst which promotes the reaction of the isocyanate groups with themselves. In this way, dimers, in particular, and trimers of the isomer in question are obtained. It is likewise possible to obtain compounds of the carbodiimide type.

The catalysts which can be used are well known to those skilled in the art. Examples of dimerization or trimerization catalysts which may be mentioned in particular are phosphines, Mannich bases, and basic compounds based on alkali metal or on alkaline-earth metal, such as sodium acetate, for example. As examples of catalysts which can be used to carry out a carbodiimidation, mention may be made of phospholine oxides. Obviously, these two lists should not be considered as exhaustive.

It is likewise possible to place the mixture to be treated in contact with a nucleophilic agent.

All the compounds of this type are suitable for carrying out this reaction. Mention may be made in particular, without, however, being limited thereto, of water, hydracids, mainly such as hydrochloric acid, aliphatic or aromatic alcohols, for instance compounds of the phenol type which may or may not have hydrocarbon radical substituents, carboxylic acids, malonic esters, amines or hydroxylamines, oximes and mercaptans.

According to one particular embodiment of the invention, this conversion is carried out such that a large part of the 2,4- isomer is converted, so as to limit the conversion of the 2,6- isomer.

According to a preferred mode, the nucleophilic agents and catalysts are used such that after the reaction, the composition of the mixture of free 2,4- and 2,6-isomers is found in the crystallization bed of the 2,6-TDI isomer.

More particulary, the content of free 2,6-TDI isomer in the mixture is greater than 50%.

Thus, when a catalyst is used, the reaction progress is controlled in particular by assaying the remaining free isocyanate groups. When the desired degree of conversion is reached, the reaction is stopped by any method known to those skilled in the art, depending on the nature of the catalyst.

According to a preferred embodiment, the 2,4-isomer is converted so as to obtain a compound which can be upgraded, in particular in the standard fields of application of isocyanates.

The dimers, trimers and carbodiimides obtained by the action of a catalyst such as those mentioned previously are compounds which are well known to those skilled in the art and which are commonly used in applications such as those mentioned previously.

The use of nucleophilic agents such as water or primary amines is advantageous since it leads to the formation of groups of urea type; bonds which can be converted later into groups of the biuret type, whose use in the preparation of flexible foams in particular is well known.

The action of hydracids, mainly hydrochloric acid, is likewise advantageous since it allows access to be gained to carbamyl chlorides, which may be decomposed again to isocyanates.

By this reaction for the conversion of the 2,4-TDI isomer, it is likewise possible to obtain half-blocked compounds of the 2,4- isomer by using, in particular, nucleophilic agents of the phenol, lactam or ketoxime type. Such compounds may be intermediates of a TDI which is totally blocked, by the subsequent action of a blocking agent, identical to or different from the first agent used. Totally-blocked TDIs find an application in particular in the field of paints.

The semi-blocked compounds may likewise, by reaction with low molecular weight polyols such as glycerol or trimethylol propane, give external crosslinking agents used, for example, in electrophoresis paints. Lastly, the reaction of semi-blocked compounds with polyethers or polyesters leads to blocked prepolymers.

The reaction for the conversion of the 2,4-TDI isomer can, without discrimination, be carried out in the presence or absence of a solvent, selected from compounds which are inert towards the various constituents of the mixture and under the reaction conditions.

The solvents used should preferably be anhydrous.

Moreover, although this is not necessary, the said solvent may be chosen such that the product obtained from the conversion of the 2,4-TDI isomer is not soluble therein.

Polar or apolar solvents are particularly suitable for carrying out the reaction. Examples which may be mentioned are chlorobenzene, orthodichlorobenzene, xylene, chloronaphthalene, decahydronaphthalene, hexane and carbon tetrachloride.

It should be noted that the conversion reaction can be carried out in one or more steps.

Thus, it may be necessary to repeat this step if a composition which lies within the crystallization bed of the 2,6-TDI has not been achieved. This is desirable, for example, when the product converted increases the viscosity of the total mixture and consequently makes it difficult subsequently to separate out the by-products of the mixture comprising the free isomers. This also allows the use of excessive amounts of solvent to be avoided.

The advantage of carrying out, in several steps, this first part of the process according to the invention is to obtain a mixture which is more enriched with 2,6-TDI isomer, so as to increase the yield for the second step of the process.

The reaction is moreover carried out at a temperature whose choice depends upon the composition of the 2,4- and 2,6-TDI isomer mixture, on the presence or absence of a solvent and on the selectivity of the conversion reaction with respect to the 2,4-TDI isomer.

Thus, the reaction temperature is relatively low, in order to promote the selective conversion of the 2,4-TDI isomer, but it is preferably not lower than the crystallization point of the mixture to be treated. This temperature may moreover vary in the course of the reaction, but a person skilled in the art is capable of adjusting it.

In the particular case of a mixture comprising 65% 2,4-TDI isomer and 35% 2,6-TDI isomer, the temperature is in the region of 10° C.

The mixture, which may be in the presence of the abovementioned solvent, is placed in contact with the catalyst or the nucleophilic agent with stirring.

Once the reaction is complete, the product formed is separated from the mixture which is now enriched with 2,6-TDI isomer.

This separation may be carried out by any known means, such as filtration, separation after settling has taken place, extraction or distillation.

If a solvent has been used during the reaction, this must be removed before treatment of the mixture enriched with 2,6-TDI isomer. This process is generally performed by distillation.

The subject of the second part of the process according to the invention is the separation of the 2,6-TDI isomer from the mixture enriched with this isomer, resulting from the preceding steps.

The operation, also referred to as refining, corresponds to one or more cycles of crystallization-melting of the mixture.

The crystallization step of the cycle consists in gradually cooling the mixture to be treated from room temperature to a temperature close to that at which the mixture is in a solid form, which temperature will be referred to as the eutectic point. Such a temperature is at about −15° C. and more particularly in the region of −13° C.

The crystallization step is preferably carried out by cooling the mixture to a temperature at which the difference from the eutectic point is between 2° and 5° C.

The rate of decrease of temperature is between −0.5° and −4° C./ hour. This rate may be kept constant throughout the temperature-lowering operation. However, according to a preferred variant, this lowering is carried out in stages by increasing the rate as the temperature of the medium gets lower.

A drainage step is then carried out, which consists in keeping the temperature constant and allowing the liquid, rich in 2,4-TDI isomer and in other impurities if they exist, to flow. This liquid residue is thus extracted from the apparatus.

It should be noted that this residue can be treated by a chemical reaction such as that described previously, in order to enrich it in 2,6-TDI isomer; this mixture may then be treated together with a fresh mixture to be treated in the crystallization-melting cycles.

Generally, the duration of this step is between 30 minutes and 3 hours.

Advantageously, and so as to minimize the duration of this stage, this operation may be carried out under a slight positive pressure of an anhydrous, neutral gas, such as nitrogen or rare gases, for example.

The second step of the cycle is performed by gradually increasing the temperature of the mixture to room temperature. The temperature of the mixture is preferably increased to the melting point of 2,6-TDI.

The rate of increase of temperature is between 0.5° and 8° C./hour. Here also, this rate may be kept constant throughout the temperature-raising operation. However, according to a preferred variant, it is raised in stages by decreasing the rate as the temperature of the medium gets higher.

According to a preferred variant of the invention, the melting step is performed in two parts. The first consists of slow heating of the crystallized mass remaining in the apparatus after evacuation of the abovementioned liquid residue. In this way, the remaining fraction of this liquid residue which is found in the crystals is removed by porosity.

The liquid fraction which then flows has an average purity between that of the abovementioned residue and that of the desired final product.

It should be noted that this liquid can be upgraded in terms of quality of intermediate products, or recycled in a subsequent cycle of crystallization-melting, together with fresh mixture to be treated, or alternatively combined with the abovementioned liquid residue to be then treated by chemical reaction in accordance with that which has been described earlier.

The second part of this step consists of the rapid melting of crystals having the expected purity.

In a manner which is standard for those skilled in the art, the purity of the liquid fraction which flows can be checked by any means such as, for example, analysis of its composition or more simply by checking the temperature of the said liquid fraction. Indeed, the temperature is a function of the composition of the liquid fraction.

The duration of each of these steps is between 5 and 20 hours.

According to a particularly advantageous variant of the present invention, and more especially when a subsequent crystallization-melting cycle is carried out on fresh mixture to be treated, a chilling operation is carried out before starting this new cycle.

This consists in cooling the empty apparatus, which comprises on its walls a film enriched with 2,6-TDI isomer, derived from a preceding operation in particular, to a temperature 2° to 3° C. higher than the eutectic point, as defined above. In addition, this temperature is more particularly 6° to 10° C. lower than the temperature at which the first crystals of the mixture considered appear when the said mixture is at thermodynamic equilibrium. This temperature is a function of the composition of the mixture considered and can be determined by any means known to those skilled in the art.

The temperature is decreased very rapidly, more particularly at a rate of about −20° C./h.

This temperature is then maintained for a period of about a few tens of minutes. The temperature is then rapidly raised, for example at a rate of about 20° C./h, to a temperature 2° to 6° C. lower than that at which the first crystals of the mixture considered appear when the mixture is at thermodynamic equilibrium.

The mixture to be treated is then introduced into the apparatus.

The temperature of the mixture is then allowed to stabilize for a period of about 1 to 2 hours, before commencing the crystallization-melting cycle described above.

The crystallization-melting cycle or cycles are performed without stirring.

The crystallization-melting cycles according to the invention can be carried out in any known type of apparatus.

A so-called static apparatus may thus be used. In this case, the liquid to be treated is introduced into a vessel containing a heat exchanger with a large area relative to the volume of the vessel, fitted with a means of controlling the temperature of the walls on which the purified crystals become deposited.

It is likewise possible to carry out the cycles in a so-called dynamic apparatus. In this case, the liquid to be treated is trickled or circulated through vertical tubes, the heat-exchange fluid trickling or circulating on the other side of the tube. The mixture to be treated thus makes a large number of passages over the cold wall on which the purified crystals are deposited. This apparatus makes it possible to shorten the duration of the crystallization-melting cycles, but it is often necessary, in order to increase the yield, to carry out several successive crystallization-melting cycles on the residual and purified products obtained from the preceding step.

According to a particular embodiment of the invention, the crystallization-melting cycles are carried out in a water-free atmosphere.

The atmosphere under which the cycle is carried out is preferably chosen from dry rare gases, such as argon, or alternatively under dry nitrogen.

The pressure at which the crystallization-melting cycle is carried out is generally in the region of atmospheric pressure or slightly higher.

During the melting step, the liquid phase is separated from the crystals, which mainly comprise the 2,6-TDI isomer.

It should be noted that fresh crystallization-melting cycles can be carried out on crystals enriched with 2,6-TDI isomer, obtained after the preceding refining step, so as to improve their purity. It should be noted that the recycling, in the process according to the invention, of the liquid fractions of insufficient purity allows the yield of the latter to be increased.

The process according to the invention thus makes it possible to recover mixtures enriched with 2,6-TDI isomer, in which the composition with regard to this isomer is higher than that of the initial mixture. The process according to the invention advantageously makes it possible to obtain the 2,6-TDI isomer in a purity of at least 90% and which can be up to 99%.

Concrete but non-limiting examples of the invention will now be presented.

EXAMPLE 1

This example illustrates the first part of the process according to the invention.

A 2-liter glass reactor is used:

fitted with a jacket in which circulates a heat transfer fluid supplied by a LAUDA-type thermostatically-controlled bath, equipped with an efficient, Rushton turbomixer-type stirrer, a vertical condenser, and a dip-type supply of anhydrous HCl.

The following are loaded into this reactor:

| o-dichlorobenzene | 500 g |
|---|---|
| toluylene diisocyanate 65/35 | 500 g |

(i.e.: 1.87 mol of 2,4-TDI and 1 mol of 2,6-TDI)

After cooling the reaction mixture to 10° C., 34 g of gaseous hydrochloric acid (0.931 mol) are introduced over 1 hour with stirring. The temperature of the reaction mixture is maintained between 10° and 12° C.

A solid-liquid two-phase mixture is rapidly formed, which becomes thick at the end of the addition of the hydrochloric acid.

The reaction mixture is filtered. The solid is washed with hexane and dried at room temperature under vacuum.

The following are thus obtained:

a solid phase consisting of:

189.5 g of carbamyl 4-monochloride (0.90 mol of TDI)

4.2 g of carbamyl 2-monochloride (0.02 mol of TDI)

The result is determined by IR spectrometry, after dissociation of the carbamyl chlorides, on the corresponding toluylene diisocyanates.

a liquid Phase having the following composition:

| o-dichlorobenzene | 480 g |
|---|---|
| 2,4-toluylene diisocyanate | 168.4 g |
|  | (0.97 mol) |
| 2,6-toluylene diisocyanate | 170.5 g |
|  | (0.98 mol) |

The composition of the mixture of TDI isomers is 50/50, determined by IR spectrometry.

The same operation is repeated with the liquid phase obtained above, to which are added 34 g of hydrochloric acid while maintaining the temperature at about 10° C.

After filtration, the following are obtained:

a solid Phase consisting of:

153.2 g of TDI carbamyl 4-monochloride (0.73 mol)

6.3 g of TDI carbamyl monochloride (0.03 mol)

a liquid Phase having the following composition:

| o-dichlorobenzene | 460 g |
|---|---|
| 2,4-TDI | 41.8 g (0.24 mol) |
| 2,6-TDI | 165.3 g (0.95 mol) |

The composition of the mixture is 20/80 with respect to 2,4-/2,6-isomers.

After elimination of the o-dichlorobenzene by distillation, 205 g of 2,4-/2,6-TDI mixture are obtained comprising 80% 2,6-TDI isomer.

A mixture of the 2 TDI isomers which lies in the crystallization bed of the 2,6- isomer is thus obtained.

Comment: The carbamyl chloride mixture may undergo dehydrochlorination to give a 97/3 2,4-TDI/2,6-TDI mixture.

EXAMPLE 2

This example illustrates the second part of the process according to the invention.

A static refiner with a working capacity of 300 ml is used, this refiner consisting of a jacketed stainless-steel cylinder 50 mm in diameter and 40 mm in height:

equipped with an automatic base valve and a jacket having its own thermostatic-control circuit, fitted with an automated collector on a balance, supplied by a programmable heating or cooling circuit, and governed by programmable automation which includes a data acquisition centre (temperature of the product and of the heat transfer fluid, masses of the fractions and times).

The apparatus functions under a slight positive pressure of argon. 154 g of the mixture obtained in Example 1 are loaded into this refiner.

The isomer mixture is crystallized, after seeding the crystallization at −4.7° C., between 3.7° C. and −10.8° C. over 14 hours, including the final temperature stabilization and the removal of the liquid residue.

The melting, including the slow heating, is carried out over 15 hours between −10.8° C. and 19.2° C.

7 fractions are isolated during the melting, which includes an increasing amount of 2,6-TDI isomer (determined by analysis).

It is observed that, by combining certain fractions, 55% of the charge recovered has a 2,6-TDI titre in the region of 95%, or that by combining other fractions, 20% of the charge recovered has a 2,6-TDI content of 99%.

EXAMPLE 3

Into a 1-liter glass reactor equipped:

with an efficient frame-type stirrer, with a 250-ml dropping funnel, with a vertical condenser, with a refrigeration system, and under an anhydrous atmosphere, are loaded:

toluylene diisocyanate 65/35 870 g (i.e. 3.25 mol of 2,4-TDI and 1.75 mol of 2,6-TDI After cooling the TDI mixture to a temperature between 8° C. and 10° C., 216 g of methyl ethyl ketoxime are run in over 1 h 30, while maintaining the temperature at this value.

A viscous homogeneous liquid is obtained, which is distilled under vacuum.

The following are thus obtained:

384 g of distillate composed of 203.5 g of 2,4-TDI (1.17 mol) and 180.5 g of 2,6-TDI (1.04 mol).

The composition of this mixture corresponds to 53% 2,4-TDI and 47% 2,6-TDI.

674 g of viscous liquid having the following composition:

| | |
|---|---|
| free TDI (2,4- + 2,6-) | 99.8 g (0.57 mol) |
| semi-blocked TDI | 440.89 g (1.69 mol) |
| totally blocked TDI | 111.2 g (0.32 mol) |
| heavy fractions | 22.2 g |

(results obtained by exclusion-diffusion chromatography/Fourier transform IR).

The same operation is repeated with the distillate obtained above to which are added 87 g of methyl ethyl ketoxime (1 mol) over 40 minutes at a temperature in the region of 10° C.

A viscous homogeneous liquid is obtained, which is distilled.

The following are thus obtained:

193 g of distillate composed of 75.3 g of 2,4-TDI (0.43 mol) and 117.7 g of 2,6-TDI (0.68 mol), i.e. a mixture of T 39.

264 g of a mixture of viscous compounds having the following composition:

| | |
|---|---|
| free TDI (2,4- + 2,6-) | 30.1 g (0.17 mol) |
| semi-blocked TDI | 146.5 g (0.56 mol) |
| totally blocked TDI | 49.6 g (0.14 mol) |
| heavy fractions | 37.8 g |

The yield for the 2 steps relative to the 2,6-TDI recovered/ 2,6-TDI engaged is (0.68×100)/1.75=39%.

A mixture of the 2 TDI isomers is obtained, lying in the crystallization bed of the 2,6- isomer. The crystallization-melting cycle according to Example 2 was repeated and allows 99% pure 2,6- isomer to be obtained.

EXAMPLE 4

This example illustrates the second part of the process according to the invention.

A static refiner with a working capacity of 4 liters is used, this refiner consisting of a jacketed stainless-steel cylinder 55 mm in diameter and 1600 mm in height:

equipped with an automatic base valve and a jacket having its own thermostatic-control circuit, fitted with an automated collector on a balance, supplied by a programmable heating or cooling circuit, and governed by programmable automation which includes a data acquisition centre (temperature of the product and of the heat transfer fluid, masses of the fractions and times).

The apparatus functions under a slight positive pressure of argon. 4830 g of a mixture containing 78.6% 2,6-TDI are loaded into this refiner.

The damp wall of the empty apparatus is chilled to a temperature in the region of −4° C.

The mixture to be treated is then loaded into the apparatus.

The crystallization phase is carried out between 6.1° and −10.5° C. over 10.5 hours, with a period of 2 hours to stabilize the temperature of the mixture at −10.5° C.

The residual liquid is then eliminated. This represents a 2,6-TDI purity of 47.8%.

The mixture is heated over 12 hours, increasing the temperature from −10.5° to 16.7° C.

The liquid fraction recovered has a 2,6-TDI purity of 76.6%.

The final melting takes place over 1 hour, increasing the temperature from 16.7° to 21° C.

A mass representing 34% of the initial charge is recovered in a 2,6-TDI purity of 99.2%.

What is claimed is:

1. A process for the production of a 2,6-toluylene diisocyanate isomer from a mixture of 2,4- and 2,6-isomers of toluylene diisocyanate, wherein said mixture, comprising at least 50% 2,6-toluylene diisocyanate, is subjected to at least one cycle of crystallization-melting, comprising the following steps:

a crystallization step is carried out by lowering the temperature to a temperature close to that at which the mixture is in a solid form;

a drainage is carried out, which consists in keeping the temperature constant and in allowing the liquid to flow; and the mixture is melted by raising the temperature from the temperature close to that at which the mixture is in a solid form, up to the melting point of the 2,6- isomer.

2. A process according to claim 1, wherein the mixture is melted by raising the temperature from about −15° C.

3. A process according to claim 1, wherein the crystallization step is carried out by lowering the temperature to a temperature to about −15° C.

4. A process for the production of the 2,6-toluylene diisocyanate isomer from a mixture of 2,4- and 2,6-isomers of toluylene diisocyanate, wherein said mixture, comprising at least 50% 2,4-toluylene diisocyanate, is placed in contact with a compound or a catalyst which is capable of converting part of the 2,4-toluylene diisocyanate isomer present, and wherein the 2,4-isomer which has reacted is separated out, then the resulting mixture is subjected to at least one cycle of crystallization-melting.

5. A process according to claim 4, wherein said compound is selected from the group consisting of nucleophilic agents, hydracids, aliphatic alcohols, aromatic alcohols, carboxylic acids, malonic esters, amines, hydroxylamines and oximes.

6. A process according to claim 4, wherein said catalyst is selected from the group consisting of phosphines, Mannich bases, basic compounds based on alkali metal, basic compounds based on alkaline-earth metal and phospholine oxides.

7. A process according to claim 4, wherein the mixture is placed in contact in the presence of a polar or apolar solvent.

8. A process according to claim 7, wherein before carrying out the first crystallization-melting cycle and after elimination of the 2,4- isomer which has reacted, the solvent is removed.

9. A process according to claim 1, wherein the crystallization-melting cycle is carried out under a water-free atmosphere.

10. A process according to claim 4, wherein the crystallization-melting cycle is carried out under a water-free atmosphere.

11. A process according to claim 1, wherein the crystallization step is carried out by lowering the temperature to a temperature at which the difference from the temperature at which the mixture is in a solid form is between 2° and 5° C.

12. A process according to claim 4, wherein the crystallization step is carried out by lowering the temperature to a temperature at which the difference from the temperature at which the mixture is in a solid form is between 2° and 5° C.

13. A process according to claim 1, wherein the rate of decrease of temperature in the crystallization step is between −0.5° and −4° C./hour.

14. A process according to claim 4, wherein the rate of decrease of temperature in the crystallization step is between −0.5° and −4° C./hour.

15. A process according to claim 1, wherein the rate of increase of temperature in the melting step is between 0.5° and 8° C./hour.

16. A process according to claim 1, wherein the rate of increase of temperature in the melting step is between 0.5° and 8° C./hour.

17. A process according to claim 14, wherein prior to the crystallization step, a chilling step is further carried out at a temperature 2° to 3° C. higher than the temperature at which the mixture is in a solid form, and 6° to 10° C. lower than the temperature at which the first crystals of the mixture appear when it is at thermodynamic equilibrium.

18. A process according to claim 15, wherein prior to the crystallization step, a chilling step is further carried out at a temperature 2° to 3° C. higher than the temperature at which the mixture is in a solid form, and 6° to 10° C. lower than the temperature at which the first crystals of the mixture appear when it is at thermodynamic equilibrium.

* * * * *